US009486229B2

(12) United States Patent
Laufer

(10) Patent No.: US 9,486,229 B2
(45) Date of Patent: Nov. 8, 2016

(54) METHODS AND DEVICES FOR EXCISION OF TISSUE

(75) Inventor: Michael D. Laufer, Menlo Park, CA (US)

(73) Assignee: Broncus Medical Inc., San Jose, CA (US)

( * ) Notice: Subject to any disclaimer, the term of this patent is extended or adjusted under 35 U.S.C. 154(b) by 0 days.

(21) Appl. No.: 13/470,069

(22) Filed: May 11, 2012

(65) Prior Publication Data

US 2013/0041373 A1    Feb. 14, 2013

Related U.S. Application Data

(63) Continuation-in-part of application No. 13/107,720, filed on May 13, 2011, and a continuation-in-part of application No. 13/107,759, filed on May 13, 2011.

(60) Provisional application No. 61/486,206, filed on May 13, 2011, provisional application No. 61/485,621, filed on May 13, 2011.

(51) Int. Cl.
  *A61B 17/22*  (2006.01)
  *A61B 18/14*  (2006.01)
  (Continued)

(52) U.S. Cl.
  CPC .............. *A61B 17/22* (2013.01); *A61B 18/14* (2013.01); *A61B 90/13* (2016.02); *A61B 5/06* (2013.01);
  (Continued)

(58) Field of Classification Search
  CPC  A61B 18/14; A61B 18/1492; A61B 14/082; A61B 2018/00577; A61B 2018/1213; A61B 2018/1425; A61B 2018/1407; A61B 2018/202; A61B 2018/00601; A61B 5/06; A61B 17/3209; A61B 17/221; A61B 17/3478; A61B 17/0293; A61B 17/0401; A61B 2019/461; A61B 2019/5255; A61B 2019/5445; A61B 2019/5278; A61B 2019/5251; A61B 2019/5257; A61B 2017/320056; A61B 2017/00809; A61B 2017/0427; A61B 2017/22042; A61B 2017/0464; A61B 2017/0417; A61B 2017/00867; A61B 2017/22034; A61B 2017/0419; A61B 1/2676; A61B 1/01; A61B 1/313; A61B 1/00082
  USPC .................. 606/47, 110, 113, 114, 115, 127
  See application file for complete search history.

(56) References Cited

U.S. PATENT DOCUMENTS

| 2,127,903 A | 8/1938 | Bowen |
| 3,174,851 A | 3/1965 | Buehler et al. |

(Continued)

FOREIGN PATENT DOCUMENTS

| EP | 0316789 A2 | 5/1989 |
| EP | 0347098 A2 | 12/1989 |

(Continued)

OTHER PUBLICATIONS

Choong, C., et al., "Feasibility and safety of airway bypass stent placement and influence of topical mitomycin C on stent patency," *J. Thorac. Cardiovasc Surg.*, 129:632-638, 2005.

(Continued)

*Primary Examiner* — Julian W Woo
*Assistant Examiner* — Lucas Paez
(74) *Attorney, Agent, or Firm* — Levine Bagade Han LLP

(57) ABSTRACT

Various apparatus and methods for excising tissue are described therein. In certain variations, a method of excising a target tissue mass from a subject, may include advancing an elongate instrument having an opening at its distal end into a subject. A cutting element, e.g., a snare or loop, may be advanced from the distal end of the elongate instrument, wherein the cutting element may be configured to cut tissue. The cutting element may be positioned near the target tissue mass. The cutting element may be actuated, e.g., expanded or deployed, and may perform energy based or mechanical cutting of a section of tissue encapsulating the target tissue mass. The cut section of tissue and the target tissue mass encapsulated therein may be removed from the subject.

17 Claims, 7 Drawing Sheets

(51) Int. Cl.
*A61B 18/08* (2006.01)
*A61B 18/00* (2006.01)
*A61B 18/12* (2006.01)
*A61B 5/06* (2006.01)

(52) U.S. Cl.
CPC .......... *A61B 18/082* (2013.01); *A61B 18/1492* (2013.01); *A61B 2017/22034* (2013.01); *A61B 2018/00577* (2013.01); *A61B 2018/00601* (2013.01); *A61B 2018/1213* (2013.01); *A61B 2018/1425* (2013.01)

(56) References Cited

U.S. PATENT DOCUMENTS

| | | |
|---|---|---|
| 3,351,463 A | 11/1967 | Rozner et al. |
| 3,406,685 A | 10/1968 | May |
| 3,433,226 A | 3/1969 | Boyd |
| 3,490,457 A | 1/1970 | Peterson |
| 3,556,079 A | 1/1971 | Omizo |
| 3,565,062 A | 2/1971 | Kuris |
| 3,617,060 A | 11/1971 | Lezzi |
| 3,707,151 A | 12/1972 | Jackson |
| 3,753,700 A | 8/1973 | Harrison et al. |
| 3,779,234 A | 12/1973 | Eggleton et al. |
| 3,823,717 A | 7/1974 | Pohlman et al. |
| 3,828,790 A * | 8/1974 | Curtiss et al. ................ 606/113 |
| 3,874,388 A | 4/1975 | King et al. |
| 3,889,688 A | 6/1975 | Eamkaow |
| 3,942,530 A | 3/1976 | Northeved |
| 4,249,539 A | 2/1981 | Vilkomerson et al. |
| 4,249,541 A | 2/1981 | Pratt |
| 4,319,580 A | 3/1982 | Colley et al. |
| 4,324,235 A | 4/1982 | Beran |
| 4,327,739 A | 5/1982 | Chmiel et al. |
| 4,332,254 A | 6/1982 | Lundquist |
| 4,355,426 A | 10/1982 | MacGregor |
| 4,407,294 A | 10/1983 | Vilkomerson |
| 4,431,006 A | 2/1984 | Trimmer et al. |
| 4,469,142 A | 9/1984 | Harwood |
| 4,493,320 A * | 1/1985 | Treat ............................... 606/47 |
| 4,503,569 A | 3/1985 | Dotter |
| 4,534,761 A | 8/1985 | Raible |
| 4,538,606 A | 9/1985 | Whited |
| 4,538,618 A | 9/1985 | Rosenberg et al. |
| 4,582,067 A | 4/1986 | Silverstein et al. |
| 4,583,969 A | 4/1986 | Mortensen |
| 4,622,968 A | 11/1986 | Persson |
| 4,655,771 A | 4/1987 | Wallsten |
| 4,658,817 A | 4/1987 | Hardy |
| 4,674,498 A | 6/1987 | Stasz |
| 4,676,782 A | 6/1987 | Yamamoto et al. |
| 4,682,596 A | 7/1987 | Bales et al. |
| 4,687,482 A | 8/1987 | Hanson |
| 4,702,252 A | 10/1987 | Brooks et al. |
| 4,706,689 A | 11/1987 | Man |
| 4,750,902 A | 6/1988 | Wuchinich et al. |
| 4,753,236 A | 6/1988 | Healey |
| 4,757,821 A | 7/1988 | Snyder |
| 4,757,822 A | 7/1988 | Di Giuliomaria et al. |
| 4,767,627 A | 8/1988 | Caldwell et al. |
| 4,769,031 A | 9/1988 | McGough et al. |
| 4,770,185 A | 9/1988 | Silverstein et al. |
| 4,771,788 A | 9/1988 | Millar |
| 4,773,413 A | 9/1988 | Hussein et al. |
| 4,781,676 A | 11/1988 | Schweighardt et al. |
| 4,785,402 A | 11/1988 | Matsuo et al. |
| 4,795,465 A | 1/1989 | Marten |
| 4,802,476 A | 2/1989 | Noerenberg et al. |
| 4,807,634 A | 2/1989 | Enjoji et al. |
| 4,808,153 A | 2/1989 | Parisi |
| 4,834,102 A | 5/1989 | Schwarzchild et al. |
| 4,855,563 A | 8/1989 | Beresnev et al. |
| 4,862,874 A | 9/1989 | Kellner |
| 4,869,268 A | 9/1989 | Yoon |
| 4,870,953 A | 10/1989 | Don Micheal et al. |
| 4,887,606 A | 12/1989 | Yock et al. |
| 4,892,098 A | 1/1990 | Sauer |
| 4,892,099 A | 1/1990 | Ohkawa et al. |
| 4,899,757 A | 2/1990 | Pope, Jr. et al. |
| 4,917,097 A | 4/1990 | Proudian et al. |
| 4,920,954 A | 5/1990 | Alliger et al. |
| 4,921,483 A | 5/1990 | Wijay et al. |
| 4,924,863 A | 5/1990 | Sterzer |
| 4,930,525 A | 6/1990 | Palestrant |
| 4,936,281 A | 6/1990 | Stasz |
| 4,955,377 A | 9/1990 | Lennox et al. |
| 4,957,508 A | 9/1990 | Kaneko et al. |
| 4,966,162 A | 10/1990 | Wang |
| 4,967,753 A | 11/1990 | Haase et al. |
| 4,973,301 A | 11/1990 | Nissenkorn |
| 4,976,690 A | 12/1990 | Solar et al. |
| 4,977,898 A | 12/1990 | Schwarzschild et al. |
| 4,991,602 A | 2/1991 | Amplatz |
| 5,002,058 A | 3/1991 | Martinelli |
| 5,030,201 A | 7/1991 | Palestrant |
| 5,042,981 A | 8/1991 | Gross |
| 5,047,026 A | 9/1991 | Rydell |
| 5,054,483 A | 10/1991 | Marten et al. |
| 5,061,275 A | 10/1991 | Wallsten et al. |
| 5,064,435 A | 11/1991 | Porter |
| 5,069,664 A | 12/1991 | Guess et al. |
| 5,081,993 A | 1/1992 | Kitney et al. |
| 5,100,423 A | 3/1992 | Fearnot |
| 5,102,417 A | 4/1992 | Palmaz |
| 5,105,816 A | 4/1992 | Shimura et al. |
| 5,105,817 A | 4/1992 | Uchibori et al. |
| 5,123,917 A | 6/1992 | Lee |
| 5,125,926 A | 6/1992 | Rudko et al. |
| 5,127,917 A | 7/1992 | Niederhauser et al. |
| 5,131,394 A | 7/1992 | Gehlbach |
| 5,145,684 A | 9/1992 | Liversidge et al. |
| 5,148,809 A | 9/1992 | Biegeleisen-Knight et al. |
| 5,155,435 A | 10/1992 | Kaufman et al. |
| 5,170,793 A | 12/1992 | Takano et al. |
| 5,178,635 A | 1/1993 | Gwon et al. |
| 5,190,528 A | 3/1993 | Fonger et al. |
| 5,201,316 A | 4/1993 | Pomeranz et al. |
| 5,201,741 A * | 4/1993 | Dulebohn ..................... 606/113 |
| 5,209,721 A | 5/1993 | Wilk |
| 5,220,924 A | 6/1993 | Frazin |
| 5,226,421 A | 7/1993 | Frisbie et al. |
| 5,234,447 A | 8/1993 | Kaster et al. |
| 5,238,027 A | 8/1993 | Lee |
| 5,246,011 A | 9/1993 | Caillouette |
| 5,246,014 A | 9/1993 | Williams et al. |
| 5,254,112 A | 10/1993 | Sinofsky et al. |
| 5,257,990 A | 11/1993 | Nash |
| 5,259,385 A | 11/1993 | Miller et al. |
| 5,261,409 A | 11/1993 | Dardel |
| 5,263,992 A | 11/1993 | Guire |
| 5,269,326 A | 12/1993 | Verrier |
| 5,273,529 A | 12/1993 | Idowu |
| 5,275,166 A | 1/1994 | Vaitekunas et al. |
| 5,282,799 A | 2/1994 | Rydell |
| 5,282,824 A | 2/1994 | Gianturco |
| 5,287,861 A | 2/1994 | Wilk |
| 5,295,484 A | 3/1994 | Marcus et al. |
| 5,299,578 A | 4/1994 | Rotteveel et al. |
| 5,304,200 A | 4/1994 | Spaulding |
| 5,309,915 A | 5/1994 | Ember |
| 5,311,871 A | 5/1994 | Yock |
| 5,313,950 A | 5/1994 | Ishikawa et al. |
| 5,316,001 A | 5/1994 | Ferek-Petric et al. |
| 5,318,564 A | 6/1994 | Eggers |
| 5,320,106 A | 6/1994 | Tanaka |
| 5,330,500 A | 7/1994 | Song |
| 5,334,146 A | 8/1994 | Ozasa |
| 5,334,183 A | 8/1994 | Wuchinich |
| 5,334,210 A | 8/1994 | Gianturco |
| 5,338,305 A | 8/1994 | Plyley et al. |
| 5,339,289 A | 8/1994 | Erickson |
| 5,344,420 A | 9/1994 | Hilal et al. |
| 5,351,693 A | 10/1994 | Taimisto et al. |
| 5,363,852 A | 11/1994 | Sharkawy |

(56) References Cited

U.S. PATENT DOCUMENTS

| | | |
|---|---|---|
| 5,363,853 A | 11/1994 | Lieber et al. |
| 5,366,504 A | 11/1994 | Andersen et al. |
| 5,368,035 A | 11/1994 | Hamm et al. |
| 5,372,138 A | 12/1994 | Crowley et al. |
| 5,375,602 A | 12/1994 | Lancee et al. |
| 5,377,682 A | 1/1995 | Ueno et al. |
| 5,380,316 A | 1/1995 | Aita et al. |
| 5,381,795 A | 1/1995 | Nordgren et al. |
| 5,383,460 A | 1/1995 | Jang et al. |
| 5,383,887 A | 1/1995 | Nadal |
| 5,385,148 A | 1/1995 | Lesh et al. |
| 5,389,096 A | 2/1995 | Aita et al. |
| 5,402,792 A | 4/1995 | Kimura |
| 5,409,012 A | 4/1995 | Sahatjian |
| 5,409,019 A | 4/1995 | Wilk |
| 5,411,466 A | 5/1995 | Hess |
| 5,413,601 A | 5/1995 | Keshelava |
| 5,417,697 A * | 5/1995 | Wilk et al. ................ 606/113 |
| 5,421,955 A | 6/1995 | Lau |
| 5,425,739 A | 6/1995 | Jessen |
| 5,427,107 A | 6/1995 | Milo et al. |
| 5,429,144 A | 7/1995 | Wilk |
| 5,435,314 A | 7/1995 | Dias |
| 5,441,515 A | 8/1995 | Khosravi et al. |
| 5,443,498 A | 8/1995 | Fontaine |
| 5,443,843 A | 8/1995 | Curatolo et al. |
| 5,452,733 A | 9/1995 | Sterman et al. |
| 5,454,373 A | 10/1995 | Koger et al. |
| 5,454,809 A | 10/1995 | Janssen |
| 5,456,258 A | 10/1995 | Kondo et al. |
| 5,458,120 A | 10/1995 | Lorraine |
| 5,464,016 A | 11/1995 | Nicholas et al. |
| 5,465,726 A | 11/1995 | Dickinson et al. |
| 5,466,242 A | 11/1995 | Mori |
| 5,470,308 A | 11/1995 | Edwards et al. |
| 5,474,075 A | 12/1995 | Goldberg et al. |
| 5,474,543 A | 12/1995 | McKay |
| 5,484,416 A | 1/1996 | Gittings |
| 5,485,841 A | 1/1996 | Watkin et al. |
| 5,500,012 A | 3/1996 | Brucker et al. |
| 5,505,088 A | 4/1996 | Chandraratna et al. |
| 5,509,900 A | 4/1996 | Kirkman |
| 5,514,154 A | 5/1996 | Lau et al. |
| 5,520,684 A | 5/1996 | Imran |
| 5,522,822 A | 6/1996 | Phelps et al. |
| 5,524,630 A | 6/1996 | Crowley |
| 5,527,292 A | 6/1996 | Adams et al. |
| 5,527,324 A | 6/1996 | Krantz et al. |
| 5,531,780 A | 7/1996 | Vachon |
| 5,536,240 A | 7/1996 | Edwards et al. |
| 5,540,713 A | 7/1996 | Schnepp-Pesch et al. |
| 5,545,195 A | 8/1996 | Lennox et al. |
| 5,545,208 A | 8/1996 | Wolf et al. |
| 5,545,210 A | 8/1996 | Hess et al. |
| 5,554,118 A | 9/1996 | Jang |
| 5,554,152 A | 9/1996 | Aita et al. |
| 5,554,181 A | 9/1996 | Das |
| 5,555,886 A | 9/1996 | Weng et al. |
| 5,562,922 A | 10/1996 | Lambert |
| 5,564,434 A | 10/1996 | Halperin et al. |
| 5,571,086 A | 11/1996 | Kaplan et al. |
| 5,571,180 A | 11/1996 | Blom |
| 5,573,531 A | 11/1996 | Gregory |
| 5,575,815 A | 11/1996 | Slepian et al. |
| 5,575,818 A | 11/1996 | Pinchuk |
| 5,588,432 A | 12/1996 | Crowley |
| 5,593,417 A | 1/1997 | Rhodes |
| 5,593,442 A | 1/1997 | Klein |
| 5,596,989 A | 1/1997 | Morita |
| 5,607,444 A | 3/1997 | Lam |
| 5,615,679 A | 4/1997 | Ri et al. |
| 5,616,608 A | 4/1997 | Kinsella et al. |
| 5,618,301 A | 4/1997 | Hauenstein et al. |
| 5,629,678 A | 5/1997 | Gargano et al. |
| 5,629,687 A | 5/1997 | Sutton et al. |
| 5,630,837 A | 5/1997 | Crowley |
| D380,266 S | 6/1997 | Boatman et al. |
| 5,638,819 A | 6/1997 | Manwaring et al. |
| 5,645,559 A | 7/1997 | Hachtman et al. |
| 5,647,871 A | 7/1997 | Levine et al. |
| 5,653,746 A | 8/1997 | Schmitt |
| 5,655,548 A | 8/1997 | Nelson et al. |
| 5,658,279 A | 8/1997 | Nardella et al. |
| 5,658,280 A | 8/1997 | Issa |
| 5,672,172 A | 9/1997 | Zupkas |
| 5,674,242 A | 10/1997 | Phan et al. |
| 5,674,277 A | 10/1997 | Freitag |
| 5,674,298 A | 10/1997 | Levy et al. |
| 5,678,555 A | 10/1997 | O'Connell |
| 5,682,880 A | 11/1997 | Brain |
| 5,693,085 A | 12/1997 | Buirge et al. |
| 5,702,418 A | 12/1997 | Ravenscroft |
| 5,704,361 A | 1/1998 | Seward et al. |
| 5,713,949 A | 2/1998 | Jayaraman |
| 5,716,393 A | 2/1998 | Lindenberg et al. |
| 5,718,701 A | 2/1998 | Shai et al. |
| 5,720,735 A | 2/1998 | Dorros |
| 5,725,521 A | 3/1998 | Mueller |
| 5,725,547 A | 3/1998 | Chuter |
| 5,725,572 A | 3/1998 | Lam et al. |
| 5,728,068 A | 3/1998 | Leone et al. |
| 5,733,301 A | 3/1998 | Forman |
| 5,736,642 A | 4/1998 | Yost et al. |
| 5,741,234 A | 4/1998 | Aboul-Hosn |
| 5,741,333 A | 4/1998 | Frid |
| 5,746,767 A | 5/1998 | Smith |
| 5,752,518 A | 5/1998 | McGee et al. |
| 5,755,769 A | 5/1998 | Richard et al. |
| 5,755,778 A | 5/1998 | Kleshinski |
| 5,759,174 A | 6/1998 | Fischell et al. |
| 5,759,769 A | 6/1998 | Sia et al. |
| 5,762,638 A | 6/1998 | Shikani et al. |
| 5,779,642 A | 7/1998 | Nightengale |
| 5,782,762 A | 7/1998 | Vining |
| 5,792,119 A | 8/1998 | Marx |
| 5,795,325 A | 8/1998 | Valley et al. |
| 5,797,920 A | 8/1998 | Kim |
| 5,807,261 A | 9/1998 | Benaron et al. |
| 5,810,008 A | 9/1998 | Dekel et al. |
| 5,810,836 A | 9/1998 | Hussein et al. |
| 5,819,723 A | 10/1998 | Joseph |
| 5,824,046 A | 10/1998 | Smith et al. |
| 5,824,048 A | 10/1998 | Tuch |
| 5,830,191 A | 11/1998 | Hildwein et al. |
| 5,830,222 A | 11/1998 | Makower |
| 5,840,431 A | 11/1998 | Kall |
| 5,843,079 A | 12/1998 | Suslov |
| 5,843,158 A | 12/1998 | Lenker et al. |
| 5,843,175 A | 12/1998 | Frantzen |
| 5,846,205 A | 12/1998 | Curley et al. |
| 5,849,037 A | 12/1998 | Frid |
| 5,851,210 A | 12/1998 | Torossian |
| 5,855,597 A | 1/1999 | Jayaraman |
| 5,855,598 A | 1/1999 | Pinchuk |
| 5,860,920 A | 1/1999 | McGee et al. |
| 5,860,951 A | 1/1999 | Eggers et al. |
| 5,868,763 A | 2/1999 | Spence et al. |
| 5,868,777 A | 2/1999 | Lam |
| 5,873,904 A | 2/1999 | Ragheb et al. |
| 5,876,345 A | 3/1999 | Eaton et al. |
| 5,876,434 A | 3/1999 | Flomenblit et al. |
| 5,876,445 A | 3/1999 | Andersen et al. |
| 5,876,448 A | 3/1999 | Thompson et al. |
| 5,885,219 A | 3/1999 | Nightengale |
| 5,906,587 A | 5/1999 | Zimmon |
| 5,906,621 A * | 5/1999 | Secrest et al. ................ 606/114 |
| 5,908,448 A | 6/1999 | Roberts et al. |
| 5,911,702 A | 6/1999 | Romley et al. |
| 5,916,158 A | 6/1999 | Webster, Jr. |
| 5,919,191 A | 7/1999 | Lennox et al. |
| 5,922,019 A | 7/1999 | Hankh et al. |
| 5,935,135 A | 8/1999 | Bramfitt et al. |
| 5,938,697 A | 8/1999 | Killion et al. |
| 5,951,567 A | 9/1999 | Javier, Jr. et al. |

(56) References Cited

U.S. PATENT DOCUMENTS

| | | | |
|---|---|---|---|
| 5,954,636 A | 9/1999 | Schwartz et al. | |
| 5,954,649 A | 9/1999 | Chia et al. | |
| 5,957,849 A | 9/1999 | Munro | |
| 5,957,919 A | 9/1999 | Laufer | |
| 5,957,949 A | 9/1999 | Leonhardt et al. | |
| 5,957,974 A | 9/1999 | Thompson et al. | |
| 5,967,990 A | 10/1999 | Thierman et al. | |
| 5,968,053 A | 10/1999 | Revelas | |
| 5,968,070 A | 10/1999 | Bley et al. | |
| 5,971,767 A | 10/1999 | Kaufman et al. | |
| 5,971,980 A | 10/1999 | Sherman | |
| 5,972,017 A | 10/1999 | Berg et al. | |
| 5,976,178 A | 11/1999 | Goldsteen et al. | |
| 5,984,871 A | 11/1999 | TenHoff et al. | |
| 5,989,276 A | 11/1999 | Houser et al. | |
| 5,993,484 A | 11/1999 | Shmulewitz | |
| 5,997,547 A * | 12/1999 | Nakao et al. | 606/114 |
| 6,001,124 A | 12/1999 | Bachinski | |
| 6,002,955 A | 12/1999 | Willems et al. | |
| 6,003,517 A | 12/1999 | Sheffield et al. | |
| 6,004,269 A | 12/1999 | Crowley et al. | |
| 6,004,273 A | 12/1999 | Sakamoto et al. | |
| 6,004,319 A | 12/1999 | Goble et al. | |
| 6,007,544 A | 12/1999 | Kim | |
| 6,007,546 A * | 12/1999 | Snow et al. | 606/113 |
| 6,007,574 A | 12/1999 | Pulnev et al. | |
| 6,010,529 A | 1/2000 | Herweck et al. | |
| 6,011,995 A | 1/2000 | Guglielmi et al. | |
| 6,013,033 A | 1/2000 | Berger et al. | |
| 6,013,093 A | 1/2000 | Nott et al. | |
| 6,013,854 A | 1/2000 | Moriuchi | |
| 6,015,405 A | 1/2000 | Schwartz et al. | |
| 6,015,415 A * | 1/2000 | Avellanet | 606/113 |
| 6,019,787 A | 2/2000 | Richard et al. | |
| 6,019,789 A | 2/2000 | Dinh et al. | |
| 6,022,371 A | 2/2000 | Killion | |
| 6,024,703 A | 2/2000 | Zanelli et al. | |
| 6,024,756 A | 2/2000 | Huebsch et al. | |
| 6,030,392 A | 2/2000 | Dakov | |
| 6,032,674 A | 3/2000 | Eggers et al. | |
| 6,036,702 A | 3/2000 | Bachinski et al. | |
| 6,045,511 A | 4/2000 | Ott et al. | |
| 6,045,532 A | 4/2000 | Eggers et al. | |
| 6,048,362 A | 4/2000 | Berg | |
| 6,053,940 A | 4/2000 | Wijay | |
| 6,053,941 A | 4/2000 | Lindenberg et al. | |
| 6,059,731 A | 5/2000 | Seward et al. | |
| 6,059,811 A | 5/2000 | Pinchasik et al. | |
| 6,063,111 A | 5/2000 | Hieshima et al. | |
| 6,064,902 A | 5/2000 | Haissaguerre et al. | |
| 6,066,169 A | 5/2000 | McGuinness | |
| 6,068,638 A | 5/2000 | Makower | |
| 6,070,094 A | 5/2000 | Swanson et al. | |
| 6,074,349 A | 6/2000 | Crowley | |
| 6,074,362 A | 6/2000 | Jang et al. | |
| 6,074,416 A | 6/2000 | Berg et al. | |
| 6,080,109 A | 6/2000 | Baker et al. | |
| 6,080,182 A | 6/2000 | Shaw et al. | |
| 6,083,162 A | 7/2000 | Vining | |
| 6,093,195 A * | 7/2000 | Ouchi | 606/113 |
| 6,096,053 A | 8/2000 | Bates | |
| 6,099,563 A | 8/2000 | Zhong | |
| 6,102,887 A | 8/2000 | Altman | |
| 6,112,123 A | 8/2000 | Kelleher et al. | |
| 6,113,612 A | 9/2000 | Swanson et al. | |
| 6,117,101 A | 9/2000 | Diederich et al. | |
| 6,120,432 A | 9/2000 | Sullivan et al. | |
| 6,120,534 A | 9/2000 | Ruiz | |
| 6,120,803 A | 9/2000 | Wong et al. | |
| 6,124,523 A | 9/2000 | Banas et al. | |
| 6,129,726 A | 10/2000 | Edwards et al. | |
| 6,135,997 A | 10/2000 | Laufer et al. | |
| 6,143,019 A | 11/2000 | Motamedi et al. | |
| 6,152,937 A | 11/2000 | Peterson et al. | |
| 6,152,945 A | 11/2000 | Bachinski et al. | |
| 6,159,225 A | 12/2000 | Makower | |
| 6,162,245 A | 12/2000 | Jayaraman | |
| 6,165,127 A | 12/2000 | Crowley | |
| 6,174,323 B1 | 1/2001 | Biggs et al. | |
| 6,176,872 B1 | 1/2001 | Miksza | |
| 6,181,348 B1 | 1/2001 | Geiger | |
| 6,183,444 B1 | 2/2001 | Glines et al. | |
| 6,186,942 B1 | 2/2001 | Sullivan et al. | |
| 6,188,355 B1 | 2/2001 | Gilboa | |
| 6,190,353 B1 | 2/2001 | Makower et al. | |
| 6,197,042 B1 * | 3/2001 | Ginn et al. | 606/213 |
| 6,200,313 B1 | 3/2001 | Abe et al. | |
| 6,200,564 B1 | 3/2001 | Lamont et al. | |
| 6,206,831 B1 | 3/2001 | Suorsa et al. | |
| 6,226,543 B1 | 5/2001 | Gilboa et al. | |
| 6,231,587 B1 | 5/2001 | Makower | |
| 6,235,024 B1 | 5/2001 | Tu | |
| 6,235,054 B1 | 5/2001 | Berg et al. | |
| 6,239,705 B1 | 5/2001 | Glen | |
| 6,241,742 B1 | 6/2001 | Spence et al. | |
| 6,241,746 B1 | 6/2001 | Bosma et al. | |
| 6,245,020 B1 | 6/2001 | Moore et al. | |
| 6,245,057 B1 | 6/2001 | Sieben et al. | |
| 6,245,102 B1 | 6/2001 | Jayaraman | |
| 6,246,784 B1 | 6/2001 | Summers et al. | |
| 6,254,632 B1 | 7/2001 | Wu et al. | |
| 6,258,100 B1 | 7/2001 | Alferness et al. | |
| 6,258,115 B1 | 7/2001 | Dubrul | |
| 6,261,601 B1 | 7/2001 | Talwar et al. | |
| 6,264,690 B1 | 7/2001 | Von Oepen | |
| 6,270,515 B1 | 8/2001 | Linden et al. | |
| 6,270,524 B1 | 8/2001 | Kim | |
| 6,272,366 B1 | 8/2001 | Vining | |
| 6,273,907 B1 | 8/2001 | Laufer | |
| 6,280,457 B1 | 8/2001 | Wallace et al. | |
| 6,283,951 B1 | 9/2001 | Flaherty et al. | |
| 6,283,983 B1 | 9/2001 | Makower et al. | |
| 6,283,988 B1 | 9/2001 | Laufer et al. | |
| 6,287,290 B1 | 9/2001 | Perkins et al. | |
| 6,290,728 B1 | 9/2001 | Phelps et al. | |
| 6,292,494 B1 | 9/2001 | Baker et al. | |
| 6,293,951 B1 | 9/2001 | Alferness et al. | |
| 6,299,604 B1 | 10/2001 | Ragheb et al. | |
| 6,299,635 B1 | 10/2001 | Frantzen | |
| 6,306,096 B1 | 10/2001 | Seward et al. | |
| 6,306,097 B1 | 10/2001 | Park et al. | |
| 6,309,375 B1 | 10/2001 | Glines et al. | |
| 6,309,415 B1 | 10/2001 | Pulnev et al. | |
| 6,309,416 B1 | 10/2001 | Swanson et al. | |
| 6,325,825 B1 | 12/2001 | Kula et al. | |
| 6,328,689 B1 | 12/2001 | Gonzalez et al. | |
| 6,331,116 B1 | 12/2001 | Kaufman et al. | |
| 6,334,869 B1 | 1/2002 | Leonhardt et al. | |
| 6,335,029 B1 | 1/2002 | Kamath et al. | |
| 6,336,933 B1 | 1/2002 | Parodi | |
| 6,342,591 B1 | 1/2002 | Zamora et al. | |
| 6,343,936 B1 | 2/2002 | Kaufman et al. | |
| 6,344,053 B1 | 2/2002 | Boneau | |
| 6,346,940 B1 | 2/2002 | Fukunaga | |
| 6,355,057 B1 | 3/2002 | DeMarais et al. | |
| 6,371,964 B1 | 4/2002 | Vargas et al. | |
| 6,379,382 B1 | 4/2002 | Yang | |
| 6,380,732 B1 | 4/2002 | Gilboa | |
| 6,391,036 B1 | 5/2002 | Berg et al. | |
| 6,394,093 B1 | 5/2002 | Lethi | |
| 6,394,956 B1 | 5/2002 | Chandrasekaran et al. | |
| 6,409,686 B1 | 6/2002 | Guthrie et al. | |
| 6,411,852 B1 | 6/2002 | Danek et al. | |
| 6,428,550 B1 | 8/2002 | Vargas et al. | |
| 6,440,163 B1 | 8/2002 | Swanson et al. | |
| 6,451,048 B1 | 9/2002 | Berg et al. | |
| 6,458,153 B1 | 10/2002 | Bailey et al. | |
| 6,466,687 B1 | 10/2002 | Uppaluri et al. | |
| 6,488,673 B1 | 12/2002 | Laufer et al. | |
| 6,490,474 B1 | 12/2002 | Willis et al. | |
| 6,493,589 B1 | 12/2002 | Medhkour et al. | |
| 6,505,065 B1 | 1/2003 | Yanof et al. | |
| 6,506,408 B1 | 1/2003 | Palasis | |
| 6,508,822 B1 | 1/2003 | Peterson et al. | |

(56) References Cited

U.S. PATENT DOCUMENTS

| | | |
|---|---|---|
| 6,511,491 B2 | 1/2003 | Grudem et al. |
| 6,514,249 B1 | 2/2003 | Maguire et al. |
| 6,514,290 B1 | 2/2003 | Loomas |
| 6,516,213 B1 | 2/2003 | Nevo |
| 6,528,301 B1 | 3/2003 | Breme et al. |
| 6,533,812 B2 | 3/2003 | Swanson et al. |
| 6,551,302 B1 | 4/2003 | Rosinko et al. |
| 6,554,848 B2 | 4/2003 | Boylan et al. |
| 6,556,696 B1 | 4/2003 | Summers et al. |
| 6,558,333 B2 | 5/2003 | Gilboa et al. |
| 6,574,498 B1 | 6/2003 | Gilboa |
| 6,575,969 B1 | 6/2003 | Rittman et al. |
| 6,585,655 B2 | 7/2003 | Crowley |
| 6,593,884 B1 | 7/2003 | Gilboa et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,615,155 B2 | 9/2003 | Gilboa |
| 6,616,675 B1 | 9/2003 | Evard et al. |
| 6,620,176 B1 | 9/2003 | Peterson et al. |
| 6,623,437 B2 | 9/2003 | Hinchliffe et al. |
| 6,623,448 B2 | 9/2003 | Slater |
| 6,629,951 B2 | 10/2003 | Laufer et al. |
| 6,634,363 B1 | 10/2003 | Laufer et al. |
| 6,635,279 B2 | 10/2003 | Kolter et al. |
| 6,635,281 B2 | 10/2003 | Wong et al. |
| 6,650,923 B1 | 11/2003 | Lesh et al. |
| 6,652,577 B2 | 11/2003 | Gianotti |
| 6,652,582 B1 | 11/2003 | Stinson |
| 6,660,015 B1 | 12/2003 | Berg et al. |
| 6,663,662 B2 | 12/2003 | Pacetti et al. |
| 6,667,051 B1 | 12/2003 | Gregory |
| 6,673,084 B1 | 1/2004 | Peterson et al. |
| 6,689,803 B2 | 2/2004 | Hunter |
| 6,692,494 B1 | 2/2004 | Cooper et al. |
| 6,694,163 B1 | 2/2004 | Vining |
| 6,695,859 B1 | 2/2004 | Golden et al. |
| 6,699,256 B1 | 3/2004 | Logan et al. |
| 6,702,780 B1 | 3/2004 | Gilboa et al. |
| 6,702,829 B2 | 3/2004 | Bachinski et al. |
| 6,711,429 B1 | 3/2004 | Gilboa et al. |
| 6,712,804 B2 | 3/2004 | Roue et al. |
| 6,712,812 B2 | 3/2004 | Roschak et al. |
| 6,712,845 B2 | 3/2004 | Hossainy |
| 6,719,698 B2 | 4/2004 | Manor et al. |
| 6,719,781 B1 | 4/2004 | Kim |
| 6,730,064 B2 | 5/2004 | Ragheb et al. |
| 6,730,349 B2 | 5/2004 | Schwarz et al. |
| 6,749,576 B2 | 6/2004 | Bauer |
| 6,749,606 B2 | 6/2004 | Keast et al. |
| 6,770,070 B1 | 8/2004 | Balbierz |
| 6,773,457 B2 | 8/2004 | Ivancev et al. |
| 6,785,410 B2 | 8/2004 | Vining et al. |
| 6,790,228 B2 | 9/2004 | Hossainy et al. |
| 6,819,785 B1 | 11/2004 | Vining et al. |
| 6,829,379 B1 | 12/2004 | Knoplioch et al. |
| 6,833,814 B2 | 12/2004 | Gilboa et al. |
| 6,852,111 B1 | 2/2005 | Lieber |
| 6,866,674 B2 | 3/2005 | Galdonik et al. |
| 6,869,443 B2 | 3/2005 | Buscemi et al. |
| 6,872,183 B2 | 3/2005 | Sampson et al. |
| 6,886,558 B2 | 5/2005 | Tanaka |
| 6,890,583 B2 | 5/2005 | Chudzik et al. |
| 6,899,731 B2 | 5/2005 | Li et al. |
| 6,909,913 B2 | 6/2005 | Vining |
| 6,918,869 B2 | 7/2005 | Shaw et al. |
| 6,918,927 B2 | 7/2005 | Bates et al. |
| 6,920,882 B2 | 7/2005 | Berg et al. |
| 6,929,637 B2 | 8/2005 | Gonzalez et al. |
| 6,941,950 B2 | 9/2005 | Wilson et al. |
| 6,960,219 B2 | 11/2005 | Grudem et al. |
| 6,961,600 B2 | 11/2005 | Kohl et al. |
| 6,970,733 B2 | 11/2005 | Willis et al. |
| 6,994,713 B2 | 2/2006 | Berg et al. |
| 6,996,430 B1 | 2/2006 | Gilboa et al. |
| 6,997,189 B2 | 2/2006 | Biggs et al. |
| 7,011,094 B2 | 3/2006 | Rapacki et al. |
| 7,014,654 B2 | 3/2006 | Welsh et al. |
| 7,022,088 B2 | 4/2006 | Keast et al. |
| 7,052,501 B2 * | 5/2006 | McGuckin, Jr. ............... 606/114 |
| 7,086,398 B2 | 8/2006 | Tanaka |
| 7,149,564 B2 | 12/2006 | Vining et al. |
| 7,169,164 B2 | 1/2007 | Borillo et al. |
| 7,175,644 B2 | 2/2007 | Cooper et al. |
| 7,179,220 B2 | 2/2007 | Kukuk |
| 7,191,101 B2 | 3/2007 | Knoplioch et al. |
| 7,226,442 B2 | 6/2007 | Sheppard, Jr. et al. |
| 7,226,472 B2 | 6/2007 | Pederson, Jr. et al. |
| 7,232,409 B2 | 6/2007 | Hale et al. |
| 7,236,620 B1 | 6/2007 | Gurcan |
| 7,260,250 B2 | 8/2007 | Summers et al. |
| 7,356,367 B2 | 4/2008 | Liang et al. |
| 7,422,563 B2 | 9/2008 | Roshak et al. |
| 7,481,775 B2 | 1/2009 | Weiker et al. |
| 7,483,755 B2 | 1/2009 | Ingle et al. |
| 7,517,320 B2 | 4/2009 | Wibowo et al. |
| 7,815,590 B2 | 10/2010 | Cooper |
| 7,963,925 B1 | 6/2011 | Schecter |
| 7,985,187 B2 | 7/2011 | Wibowo et al. |
| 8,235,908 B2 | 8/2012 | Roshak et al. |
| 8,308,682 B2 | 11/2012 | Kramer et al. |
| 8,337,516 B2 | 12/2012 | Escudero et al. |
| 8,409,167 B2 | 4/2013 | Roshak |
| 8,784,400 B2 | 7/2014 | Roschak |
| 2001/0007940 A1 | 7/2001 | Tu et al. |
| 2001/0021872 A1 | 9/2001 | Bailey et al. |
| 2001/0026666 A1 | 10/2001 | Ferrera et al. |
| 2001/0027339 A1 | 10/2001 | Boatman |
| 2001/0027341 A1 | 10/2001 | Gianotti |
| 2001/0044576 A1 | 11/2001 | Vining |
| 2001/0044650 A1 | 11/2001 | Simso et al. |
| 2001/0047180 A1 | 11/2001 | Grudem et al. |
| 2001/0052344 A1 | 12/2001 | Doshi |
| 2002/0002401 A1 | 1/2002 | McGuckin et al. |
| 2002/0022833 A1 | 2/2002 | Maguire et al. |
| 2002/0028006 A1 | 3/2002 | Novak et al. |
| 2002/0028008 A1 | 3/2002 | Fan et al. |
| 2002/0032477 A1 | 3/2002 | Helmus et al. |
| 2002/0042564 A1 | 4/2002 | Cooper et al. |
| 2002/0042565 A1 | 4/2002 | Cooper et al. |
| 2002/0042622 A1 | 4/2002 | Vargas et al. |
| 2002/0049370 A1 | 4/2002 | Laufer et al. |
| 2002/0055772 A1 | 5/2002 | McGuckin et al. |
| 2002/0071902 A1 | 6/2002 | Ding et al. |
| 2002/0087153 A1 | 7/2002 | Roschak et al. |
| 2002/0091433 A1 | 7/2002 | Ding et al. |
| 2002/0111619 A1 | 8/2002 | Keast et al. |
| 2002/0111620 A1 | 8/2002 | Cooper et al. |
| 2002/0119178 A1 | 8/2002 | Levesque et al. |
| 2002/0123786 A1 | 9/2002 | Gittings et al. |
| 2002/0128647 A1 | 9/2002 | Roschak et al. |
| 2002/0131625 A1 | 9/2002 | Vining et al. |
| 2002/0133057 A1 | 9/2002 | Kukuk |
| 2002/0138074 A1 | 9/2002 | Keast et al. |
| 2002/0147462 A1 | 10/2002 | Mair |
| 2002/0161321 A1 | 10/2002 | Sweezer et al. |
| 2002/0161377 A1 | 10/2002 | Rabkin |
| 2003/0017150 A1 | 1/2003 | Torphy |
| 2003/0070676 A1 | 4/2003 | Cooper et al. |
| 2003/0070682 A1 | 4/2003 | Wilson et al. |
| 2003/0120292 A1 | 6/2003 | Park et al. |
| 2003/0130575 A1 | 7/2003 | Desai |
| 2003/0130657 A1 * | 7/2003 | Tom et al. ............... 606/47 |
| 2003/0153715 A1 | 8/2003 | Chandrasekaran |
| 2003/0204138 A1 | 10/2003 | Choi |
| 2003/0216806 A1 | 11/2003 | Togawa et al. |
| 2004/0055606 A1 | 3/2004 | Hendricksen et al. |
| 2004/0060563 A1 | 4/2004 | Rapacki et al. |
| 2004/0073155 A1 | 4/2004 | Laufer et al. |
| 2004/0073201 A1 | 4/2004 | Cooper et al. |
| 2004/0073284 A1 | 4/2004 | Bates et al. |

(56) References Cited

U.S. PATENT DOCUMENTS

| | | |
|---|---|---|
| 2004/0078054 A1 | 4/2004 | Biggs et al. |
| 2004/0093070 A1 | 5/2004 | Hojeibane et al. |
| 2004/0211434 A1 | 10/2004 | Loomas et al. |
| 2004/0220496 A1* | 11/2004 | Gonzalez ............... 600/562 |
| 2004/0220556 A1 | 11/2004 | Cooper et al. |
| 2004/0261203 A1 | 12/2004 | Dworzan |
| 2005/0016530 A1 | 1/2005 | McCutcheon et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0085801 A1 | 4/2005 | Cooper et al. |
| 2005/0096529 A1 | 5/2005 | Cooper et al. |
| 2005/0107679 A1 | 5/2005 | Geiger et al. |
| 2005/0107783 A1 | 5/2005 | Tom et al. |
| 2005/0135662 A1 | 6/2005 | Vining et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0147284 A1 | 7/2005 | Vining et al. |
| 2005/0165342 A1 | 7/2005 | Odland |
| 2005/0171527 A1 | 8/2005 | Bhola |
| 2005/0177144 A1 | 8/2005 | Phan et al. |
| 2005/0182295 A1 | 8/2005 | Soper et al. |
| 2005/0182475 A1 | 8/2005 | Jen et al. |
| 2005/0192526 A1 | 9/2005 | Biggs et al. |
| 2005/0228268 A1 | 10/2005 | Cole |
| 2005/0251202 A1 | 11/2005 | Ewers et al. |
| 2005/0261550 A1 | 11/2005 | Akimoto et al. |
| 2005/0288549 A1 | 12/2005 | Mathis |
| 2006/0023966 A1 | 2/2006 | Vining |
| 2006/0069385 A1 | 3/2006 | Lafontaine et al. |
| 2006/0116749 A1 | 6/2006 | Willink et al. |
| 2006/0135984 A1 | 6/2006 | Kramer et al. |
| 2006/0142672 A1 | 6/2006 | Keast et al. |
| 2006/0183973 A1 | 8/2006 | Kamrava |
| 2006/0254600 A1 | 11/2006 | Danek et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2007/0010438 A1 | 1/2007 | Mayo et al. |
| 2007/0016072 A1 | 1/2007 | Grunwald et al. |
| 2007/0092864 A1 | 4/2007 | Reinhardt et al. |
| 2007/0123922 A1 | 5/2007 | Cooper et al. |
| 2007/0250070 A1* | 10/2007 | Nobis et al. ............... 606/113 |
| 2007/0255304 A1 | 11/2007 | Roschak et al. |
| 2008/0009760 A1 | 1/2008 | Wibowo et al. |
| 2008/0027273 A1 | 1/2008 | Gutterman |
| 2008/0039715 A1 | 2/2008 | Wilson et al. |
| 2008/0086107 A1 | 4/2008 | Roschak |
| 2008/0097139 A1 | 4/2008 | Clerk et al. |
| 2008/0213337 A1 | 9/2008 | Hermansson et al. |
| 2008/0302359 A1 | 12/2008 | Loomas et al. |
| 2008/0312543 A1 | 12/2008 | Laufer et al. |
| 2009/0054805 A1 | 2/2009 | Boyle, Jr. |
| 2009/0076491 A1 | 3/2009 | Roschak et al. |
| 2009/0124883 A1 | 5/2009 | Wibowo et al. |
| 2009/0131765 A1 | 5/2009 | Roschak et al. |
| 2009/0143678 A1 | 6/2009 | Keast et al. |
| 2009/0163949 A1 | 6/2009 | Rolnick et al. |
| 2009/0204005 A1 | 8/2009 | Keast et al. |
| 2009/0275840 A1 | 11/2009 | Roschak et al. |
| 2009/0287087 A1 | 11/2009 | Gwerder et al. |
| 2009/0318904 A9 | 12/2009 | Cooper et al. |
| 2010/0041949 A1 | 2/2010 | Tolkowsky |
| 2010/0268316 A1 | 10/2010 | Brenneman et al. |
| 2010/0305463 A1 | 12/2010 | Macklem et al. |
| 2010/0312141 A1 | 12/2010 | Keast et al. |
| 2011/0082456 A1* | 4/2011 | Welt et al. ............... 606/45 |
| 2011/0146673 A1 | 6/2011 | Keast et al. |
| 2011/0146674 A1 | 6/2011 | Roschak |
| 2011/0251592 A1 | 10/2011 | Biggs et al. |
| 2011/0306997 A9 | 12/2011 | Roshak et al. |
| 2012/0085346 A9 | 4/2012 | Roshak |
| 2012/0089116 A9 | 4/2012 | Roshak |
| 2012/0123264 A9 | 5/2012 | Keast et al. |
| 2012/0221013 A1 | 8/2012 | Hawkins et al. |
| 2012/0232523 A1 | 9/2012 | Roshak |
| 2012/0289776 A1 | 11/2012 | Keast et al. |
| 2012/0289815 A1 | 11/2012 | Keast et al. |
| 2013/0046198 A1 | 2/2013 | Roshak et al. |
| 2013/0046296 A1 | 2/2013 | Laufer et al. |
| 2013/0123638 A1 | 5/2013 | Tom et al. |
| 2013/0123826 A1 | 5/2013 | Kramer et al. |

FOREIGN PATENT DOCUMENTS

| | | |
|---|---|---|
| EP | 0443256 A1 | 8/1991 |
| EP | 1151729 A1 | 11/2001 |
| EP | 1400204 A1 | 3/2004 |
| EP | 1485033 A2 | 12/2004 |
| JP | 2001-104315 | 4/1989 |
| JP | 2000-107178 | 4/2000 |
| WO | WO 87/05739 | 9/1987 |
| WO | WO 89/06515 | 7/1989 |
| WO | WO 90/01300 | 2/1990 |
| WO | WO 91/08706 | 6/1991 |
| WO | WO 95/02361 | 1/1995 |
| WO | WO 95/32011 | 11/1995 |
| WO | WO 96/25886 | 8/1996 |
| WO | WO 96/39914 | 12/1996 |
| WO | WO 97/17014 | 5/1997 |
| WO | WO 97/17105 | 5/1997 |
| WO | WO 98/16161 | 4/1998 |
| WO | WO 98/28035 | 7/1998 |
| WO | WO 98/48706 | 11/1998 |
| WO | WO 98/57590 | 12/1998 |
| WO | WO 99/01076 | 1/1999 |
| WO | WO 99/11182 | 3/1999 |
| WO | WO 99/25419 | 5/1999 |
| WO | WO 99/38454 | 8/1999 |
| WO | WO 99/60953 | 12/1999 |
| WO | WO 00/21461 | 4/2000 |
| WO | WO 00/27310 | 5/2000 |
| WO | WO 00/27313 | 5/2000 |
| WO | WO 00/45742 | 8/2000 |
| WO | WO 00/67825 | 11/2000 |
| WO | WO 00/72908 | 12/2000 |
| WO | WO 00/74579 | 12/2000 |
| WO | WO 01/10314 | 2/2001 |
| WO | WO 01/13839 | 3/2001 |
| WO | WO 01/28433 | 4/2001 |
| WO | WO 01/32088 | 5/2001 |
| WO | WO 01/39672 | 6/2001 |
| WO | WO 01/49213 | 7/2001 |
| WO | WO 01/54585 | 8/2001 |
| WO | WO 01/70117 | 9/2001 |
| WO | WO 01/74274 | 10/2001 |
| WO | WO 01/89366 | 11/2001 |
| WO | WO 02/00278 | 1/2002 |
| WO | WO 02/064045 | 8/2002 |
| WO | WO 02/064190 | 8/2002 |
| WO | WO 02/069823 | 9/2002 |
| WO | WO 03/020338 | 3/2003 |
| WO | WO 03/071924 | 9/2003 |
| WO | WO 03/073358 | 9/2003 |
| WO | WO 03/088820 | 10/2003 |
| WO | WO 03/097153 | 11/2003 |
| WO | WO 03/103479 | 12/2003 |
| WO | WO 2005/006963 | 1/2005 |
| WO | WO 2005/006964 | 1/2005 |
| WO | WO 2006/014731 | 2/2006 |
| WO | WO 2006/014732 | 2/2006 |
| WO | WO 2006/130821 | 12/2006 |
| WO | WO 2006/130873 | 12/2006 |
| WO | WO 2007/033379 | 3/2007 |
| WO | WO 2007/062406 | 5/2007 |

(56) References Cited

FOREIGN PATENT DOCUMENTS

| WO | WO 2008/063935 | 5/2008 |
|---|---|---|
| WO | WO 2008/109760 | 9/2008 |

OTHER PUBLICATIONS

Choong, C., et al., "Prolongaton of patency of airway bypass stents with use of drug-eluting stents," *J. Thorac. Cardiovasc. Surg.*, 131: 60-64, 2006.
Cordis Johnson & Johnson Gateway LLC: Bx Velocity Stent. Viewed at: http://www.jnjgateway.com/home.jhtm?loc=USENG&page=viewContent&contentId=fc0de00100001015&parentId=fcde00100001015&specialty=Circulatory_Disease_Management&category=Cardiac_Diagnosi_Interventions&subcategory=Stents_Balloon_Expandable Viewed on Sep. 5, 2002, 4 pages (please note p. 4 of 4 is blank).
Fessler, H., "Collateral Ventilation, the Bane of Bronchoscopic Volume Reduction," *Am J. Respir Crit. Care Med.* (editorial), 171:423-425, 2005.
Flenley, D., et al., "Factors Affecting Gas Exchange by Collateral Ventilation in the Dog," *Respiration Physiology*, 15:52-69, 1972.
Hogg, W., et al., "Gas Diffusion Across Collateral Channels," *Journal of Applied Physiology*, 33(5):568-575.
Lausberg, H., et al., "Bronchial fenestraton improves expiratory flow in emphysematous human lungs," Ann. Thorac. Surg., 75:393-398, 2003.
Macklem, P., "Collateral ventilation," *N. Engl. J. Med.*, 298(1):49-50, 1978.
Menkes, H., et al., "Influence of Surface Forces on Collateral Ventilation," *Journal of Applied Physiology*, 31(4):544-549, 1971.
Panettieri, R., "Chronic Obstructive Pulmonary Disease," *Lippincott's Pathophysiology Series: Pulmonary Pathophysiology*, pp. 93-107, Grippi, M., et al., eds., J.B. Lippincott Company, Philadelphia, PA, 1995.
Pulmonary and Critical Care Medicine. Interventional Bronchoscopy with Stent Implant: Stents. Viewed at: http://view.vcu.edu/pulm-ccm/stents.htm Viewed on Aug. 26, 2002. 2 pages.
Rendina, E., et al., "Feasibility and safety of the airway bypass procedure for patients with emphysema," *J. Thorac. Cardiovasc. Surg.*, 125:1294-1299, 2003.
Terry, P., et al., "Collateral Ventilation in Man," *The New England Journal of Medicine*, 298(1):10-15, 1978.
Wagner, E., et al., "Direct Assessment of Small Airways Reactivity in Human Subjects," *Am. J. Respir. Crit. Care Med.*, 157:447-452, 1998.
Woolcock, A., et al., "Mechanical Factors Influencing Collateral Ventilation in Human, Dog and Pig Lungs," *Journal of Applied Physiology*, 30(1):99-115, 1971.
Morrell et al, "Collateral ventilation and gas exchange in emphysema", Am J Respir Crit Care Med; (3); Sep. 1994: pp. 635-641.

\* cited by examiner

METHODS AND DEVICES FOR EXCISION OF TISSUE

CROSS-REFERENCE TO RELATED APPLICATIONS

The present application claims priority to U.S. Provisional Application No. 61/486,206 filed May 13, 2011 and U.S. Provisional Application No. 61/485,621 filed May 13, 2011; and is a continuation-in-part of U.S. application Ser. No. 13/107,720 filed May 13, 2011 and U.S. application Ser. No. 13/107,759 filed May 13, 2011, the contents of each of which are incorporated herein by reference in their entirety.

FIELD OF THE INVENTION

This application is directed to methods and devices for excising tissue. The procedures described herein may be performed in various regions of the body.

BACKGROUND

Current procedures for excising tissue involve invasive surgeries, e.g., cutting open a patient's chest to excise tissue in a lung. Other procedures involve the use of needles to remove portions of a tumor or diseased tissue. These procedures can cause complications and have their limitations. Because of the difficulties and risks associated with these current procedures, tumors are often left in place and monitored to determine whether or not they are cancerous. This exposes the patient to large amounts of radiation as well as the stress and worry of knowing a potentially lethal tumor or nodule remains in their body.

Therefore, there remains a need for more effective and efficient apparatus and methods for excising tissue in a minimally invasive fashion.

SUMMARY

Various apparatus and methods for excising tissue are described therein.

In certain variations, a method of excising a target tissue mass from a subject, may include one or more of the following steps. An elongate instrument having an opening at its distal end may be advanced into a subject. A cutting element e.g., a snare, may be advanced from the distal end of the elongate instrument, where the cutting element or snare may be configured to cut tissue. The cutting element or snare may be positioned near the target tissue mass. The cutting element or snare may be actuated, e.g., expanded or deployed, and may perform energy based or mechanical cutting of a section of tissue encapsulating the target tissue mass. The cut section of tissue and the target tissue mass encapsulated therein may be removed from the subject. In certain variations, the cutting element or snare may be advanced while energized electrically to cut tissue, expanded and/or rotated around the tissue mass while energized electrically to cut tissue, and then used without electrical activation to encapsulate or fixate onto the tissue mass to enable withdrawal of the tissue mass from the body.

In certain variations, an apparatus for excising a target tissue mass from a subject may include an elongate instrument having an opening at its distal end. The opening may be divided by a septum or divider to create a first port and a second port. An actuatable cutting element or snare may have a first portion or leg extending from the first port and a second portion or leg extending from the second port. The cutting element or snare may be configured to cut tissue and the septum or divider may be configured to support the actuatable cutting element or snare during rotation.

In certain variations, various excision methods and apparatus described herein may be guided to or near a target tissue or may access a target tissue or tumor by being advanced into and through an airway, through an opening or extra-anatomic opening created in an airway wall and to or near the target tissue or tumor beyond, at, outside or near the created opening. In other variations, the methods and apparatus described herein may be utilized to perform excision procedures in various regions of the body utilizing various access techniques.

This application is also related to the following applications 61/485,621, filed on May 13, 2011; Ser. No. 13/107,720, filed on May 13, 2011; 13/107,759, filed on May 13, 2011; 61/563,369 filed Nov. 23, 2011; Ser. No. 11/538,950 filed Oct. 5, 2006; Ser. No. 12/939,968 filed Nov. 4, 2010; Ser. No. 12/939,961 filed Nov. 4, 2010; Ser. No. 12/939,956 filed Nov. 4, 2010 and the patent application filed on the same day as the present application and titled "METHODS AND DEVICES FOR ABLATION OF TISSUE"; the contents of each of which are incorporated herein by reference in their entirety.

DETAILED DESCRIPTION

Various apparatus and methods for excising tissue in a subject are described herein. Tissue may be excised from various parts of the body, including, e.g., the lung. Various types of tissue may be excised, including, e.g., diseased tissue, tumors or nodules. In certain variations, the procedures described herein may be performed through an opening, port or channel through an airway wall.

Figure 1A:
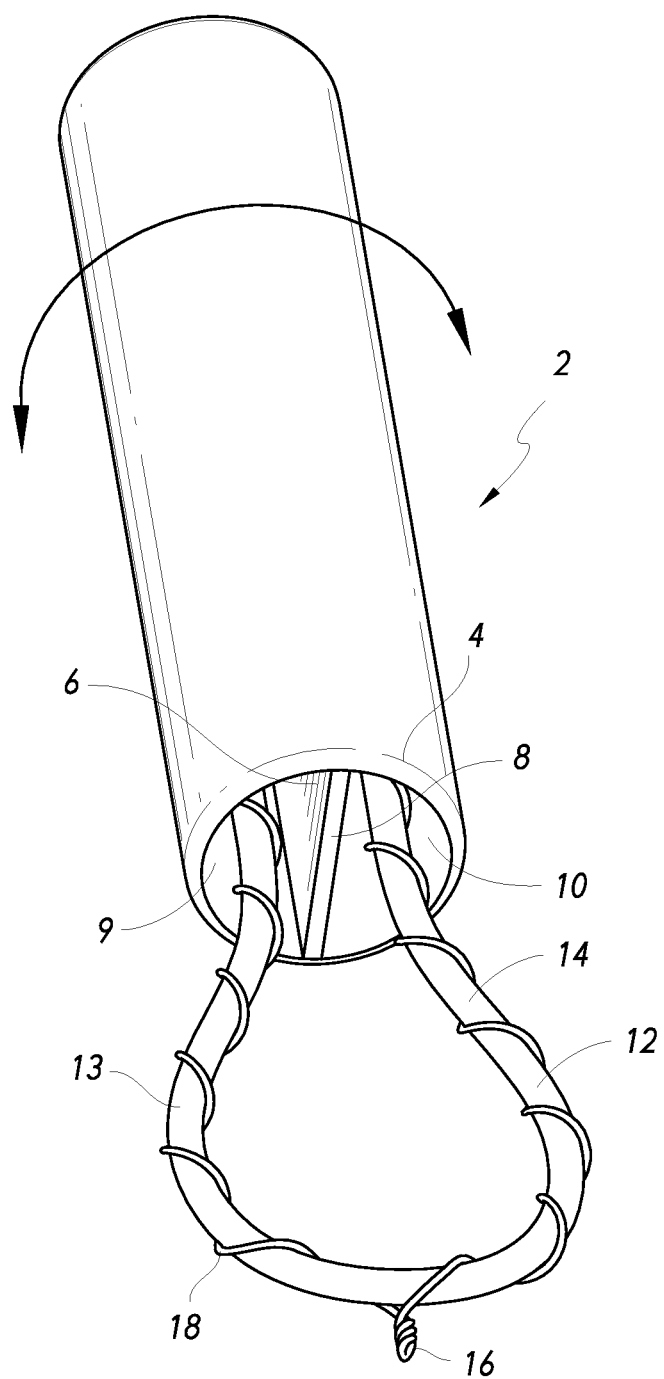
FIGS. 1A-1B illustrates various views of a variation of an apparatus for excising tissue.
Figure 1B:
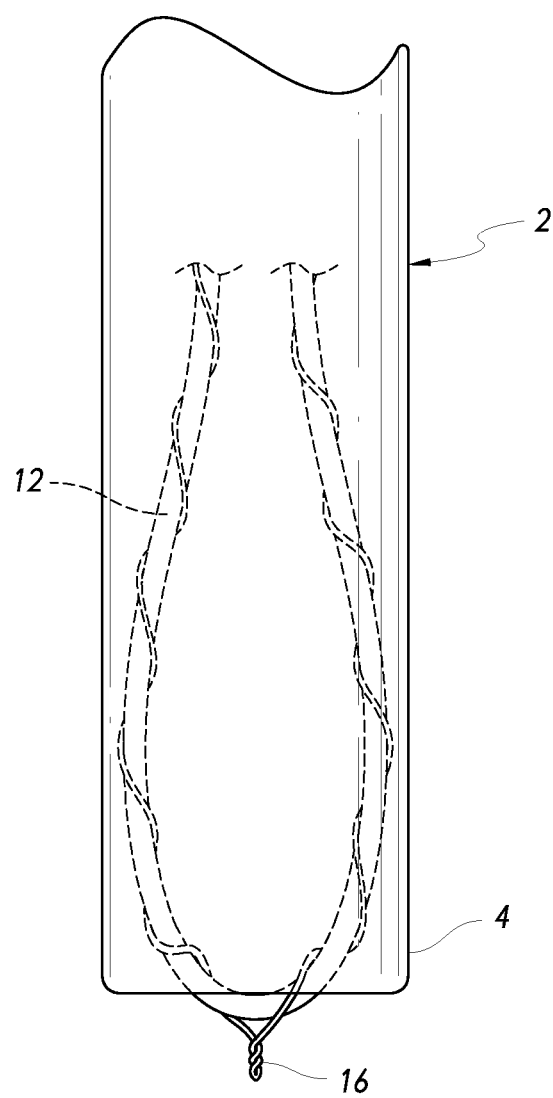

FIGS. 1A and 1B show one variation of an apparatus for excising tissue. The apparatus may include an elongate instrument 2, e.g., a rod, shaft or sheath. The elongate instrument 2 may have a proximal end and a distal end 4 or tip. The elongate instrument 2 may include one or more lumens extending from the proximal end to the distal end 4. The distal end 4 may include one or more openings 6. The distal end 4 of the elongate instrument may include a septum 8, wall or divider, which may divide the opening 6 into two or more ports, openings or holes, e.g., a first port 9 and a second port 10. The ports or holes may have a variety of shapes. For example, the septum 8 may divide the opening 6, providing two D shaped ports or circular ports.

A cutter or cutting element may be provided in or on the elongate instrument 2, e.g., at the distal end of the elongate instrument. The cutting element may be actuatable from the opening 6 at the distal end 4 of the elongate instrument 2, e.g., the cutting element may be extendable retractable, or rotatable. In certain variations, the cutting element may be in the form of a snare, loop, or other wire or cable having various configurations. The cutting element may include conductive material, such that the cutting element may be energized to deliver energy, e.g., electricity or heat, to perform the cutting of a tissue. For example, the cutting element may be an electrical cutting element having one or more electrodes through which electrical current flows, e.g., a snare or loop or partial loop electrode. The electrical cutting element may be monopolar or bipolar and utilize different wavelengths (e.g. radiofrequency) and waveforms (e.g. pulsed, continuous, or sinusoidal) of energy. In another variation, a mechanical cutting element having a sharpened edge, surface or blade may be utilized. A cutting element may have mechanical and/or energy based cutting functionality. Such cutting elements may be used separately or in combination.

FIGS. 1A and 1B show an example of a cutting element in the form of a snare 12. The snare 12 have a first portion 13, leg or member positioned in or extending from or into the first port 9 and a second portion 14, leg or member positioned in or extending from or into the second port 10. A snare is meant to include but is not limited to a loop, e.g., a partial loop, or complete loop, or other collapsible or expandable curved element or wire. The first and second portions or members 13, 14 of the snare may extend and join in an arc, loop or curved portion to form the snare 12. The snare may be constructed of a single piece of wire, cable or other material that is curved or doubled on itself or optionally, the snare may be formed from multiple pieces of wire, cable or other material. The snare 12 may include conductive material (e.g. stainless steel, nitinol, or nichrome), such that the snare may be energized to deliver energy, e.g., electricity or heat, to perform the cutting of a tissue. In certain variations the snare may be a loop or partial loop electrode. In certain variations, the snare may be a wire. The wire may have a variety of shapes, e.g., the wire may be circular or D-shaped. A D-shaped wire may provide enhanced rigidity to the wire or provide the wire with enhanced torsional strength or hoop strength. The snare may have sufficient hoop strength such that it may expand, e.g., passively or actively expand, within tissue as it cuts into tissue. In certain variations, the snare or wire may be a ribbon or have a ribbon-like shape, providing torsional rigidity to the snare or wire in the direction of rotation. The snare may or may not be operated under saline irrigation. The snare 12 may be expandable, collapsible, and/or retractable. In certain variations, the snare 12 may have a sharpened edge or surface for mechanical cutting.

A protrusion 16, e.g., a piercing member, nipple or tip, may extend from the snare 12. As shown, in FIG. 1A, the protrusion 16 may extend from a distal portion or point of the snare or from a distal turn in the snare or loop. The protrusion 16 may be used to pierce tissue, for example, to pierce through and create an opening through an airway wall. The protrusion 16 may provide concentrated or localized electron density such that the protrusion 16 may pierce, cut or form a hole through tissue. In certain variations, a wire may be twisted or bent to form the protrusion 16, creating a point or tip that can have a concentrated or increased energy density. In other variations the protrusion may have a pointed or sharpened end such that the protrusion may mechanically puncture, pierce cut or form a hole through tissue.

In certain variations, a conductive wire 18 may be wrapped around a snare 12. The wire 18 may provide points or focal points of increased or concentrated electron density along and/or on the snare 12 for cutting tissue. In certain variations, a snare having conductive properties may be utilized with or without a conductive wire or other conductive material wrapped around or positioned on the snare 12. In certain variations, a snare having a wire wrapped thereon to provide electron density focal points along the snare may require less power to perform cutting than a snare having no wire wrapped thereon. The conductive wire may be wrapped around the loop or partial loop portion of a snare and/or around the protrusion or nipple on the snare. The energized snare, protrusion, and/or wrapped wire may cut through tissue.

As shown in FIG. 1A, the distal end 4 of the elongate instrument 2 may include a septum 8, wall or divider segment, which divides the opening 6 into at least a first port 9 and a second port 10. A port is meant to include but is not limited to any opening, hole, channel or slit. The septum 8 may vary in length along the longitudinal axis of the elongate instrument and may divide at least a portion of a lumen extending from the proximal end of the elongate instrument to the opening at the distal end of the elongate instrument, providing one or more channels or tunnels therein in communication with the first and/or second ports or openings.

The septum 8 may be rigid and/or may provide support, e.g., torsional or rotational rigidity or support, to the elongate instrument. The septum 8 may support a cutter, such as a snare. Where a septum is utilized to divide the opening into a first and second port, the size of the port openings and the size of the snare wire to be received or to extend from the ports may be maximized, while the septum may be configured to still provide support, e.g., rotational or torsional support, to the snare.

In certain variations, the apparatus for excising tissue may include an elongate instrument having a flexible proximal portion that may provide the elongate instrument with flexibility and/or torquability for navigating or weaving the elongate instrument in one or more degrees of freedom, through the tortuous anatomy of a subject, e.g., through airways, and/or for rotating the elongate instrument and/or cutter or snare. For example, since the elongate instrument may be used to access airways deep within the lung, the elongate instrument may include a flexible material. The elongate instrument may be sufficiently flexible to pass through a fully articulated bronchoscope. The elongate instrument may also include a support or rigid or reinforced distal portion for supporting a snare or other cutter extending from the distal portion of the elongate instrument, e.g., to provide rotational, torsional or other support or rigidity to the cutter or snare during actuation, e.g., during rotation of the cutter or snare or in the direction of rotation.

In one variation, an apparatus for excising tissue may include a backend or a proximal portion having sufficient flexibility and torquability to navigate or weave through airways and a distal portion that includes an insulating tip and/or sufficient rigidity to provide support for a snare, loop or other cutter during rotation of the elongate instrument and/or the snare, loop or cutter. An apparatus for excising tissue may be configured to provide sufficient support such that a snare or loop may remain in an open or expanded position with sufficient energy density for cutting tissue (without shorting out) while the snare or loop is being torqued or rotated. The supportive distal portion and/or septum of the apparatus prevents the wires, first and second portions, members or legs of the snare or loop from coming together, contacting or crossing each other, or collapsing on each other, which may result in loss of electrical current density in the snare and decreased cutting functionality.

Figure 2:
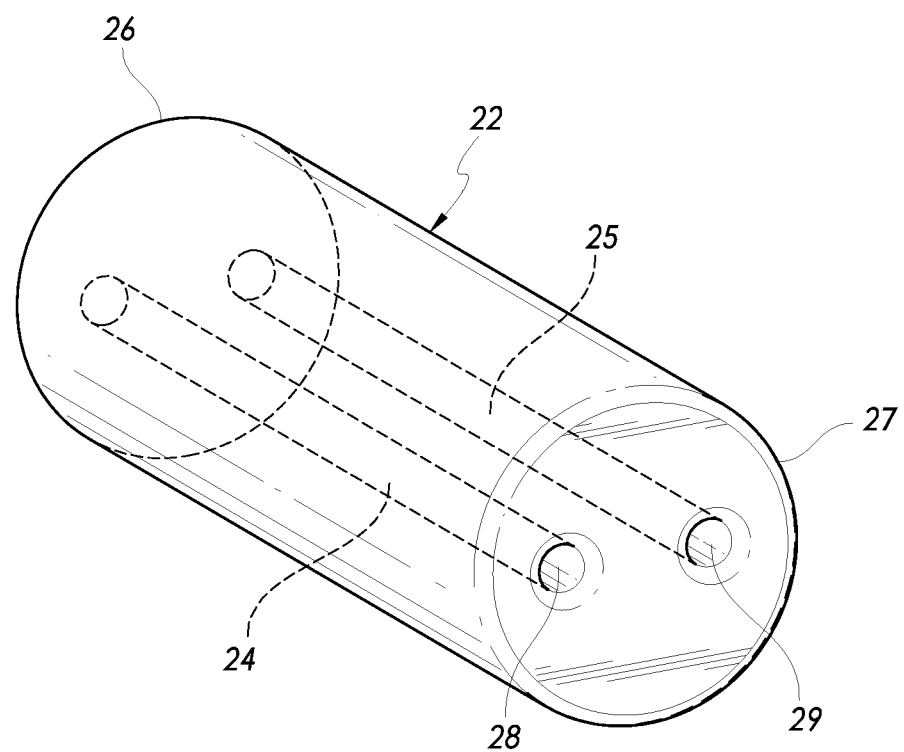
FIG. 2 illustrates a cross section of a variation of an elongate instrument of an apparatus for excising tissue.

FIG. 2 shows a cross section of another variation of an apparatus for excising tissue. The apparatus includes an elongate instrument 22 having two or more lumens 24, 25 within the elongate instrument 22, where each lumen is in communication with an opening 28, 29 at the distal end of the elongate instrument 22. For example, the lumens may extend from a proximal end 26 to a distal end 27 of the elongate instrument 22 or along any portion of the elongate instrument. A snare (not shown) may extend from the elongate instrument where a first portion or leg of the snare is positioned in or extends from a first lumen 24 and a second portion or leg of the snare is positioned in or extends from the second lumen 25.

A variety of elongate instruments, e.g., shafts, rods or sheaths, having various opening, lumen, septum or divider configurations are contemplated herein. The variations may provide a rigid, stable and/or torsional or rotational supportive distal end or portion for an elongate instrument to effect cutting of tissue and/or to allow for rotation of a cutter or snare to effectively cut tissue while preventing the snare or other loop or wire from collapsing on itself and disrupting the flow of energy through the snare, loop or wire. At least a portion of the various elongate instruments, for example, a distal portion or end, may be made from one or more materials including glass, quartz, Pyrex, Peek, ceramic, or any other material having a high melting point, which may be insulated, may withstand high temperatures, and/or provide rotational or torsional support to the cutter. The elongate instruments may be insulating. In certain variations, only the distal end or tip or distal portion of an elongate instrument is made from glass or a similar insulating material, which may provide a rigid support on the elongate instrument. An elongate instrument may also have a flexible portion or end, e.g., proximal portion or end, providing the instrument with the flexibility and maneuverability to navigate through the anatomy of a subject.

In one variation, an apparatus for excising tissue may include an insulating rod. A snare or wire loop may extend from the insulating rod. Radiofrequency (RF) energy may be used to energize the snare or wire loop. A grounding plate may also be utilized. The insulating rod may have an opening at its distal end. The opening may be divided by a septum, such that the opening looks like a theta θ. The septum divides the opening into two ports or holes, through which the snare or wire loop extends.

In use, an apparatus for excising tissue, as described herein, may perform tissue excision in a variety of ways, e.g., by electrical or mechanical cutting. A target tissue mass may be located within a subject. The elongate instrument having a cutter may be inserted into the subject. The elongate instrument may be advanced percutaneously or intraluminally or in any minimally invasive manner.

In one variation, a method for excising a target tissue mass, e.g., a tumor, from a patient's lung may include one or more of the following steps. The elongate instrument may be navigated within a lumen of an airway in the lung. The elongate instrument may be advanced to, near or in the proximity of the target tissue mass, e.g., via an opening created in an airway wall. The cutting element, e.g., a snare, loop or partial loop configuration, may be in a retracted position within the elongate instrument, and the protrusion on a distal portion of the snare may be positioned, extend or jut out through the opening at the distal end of the elongate instrument, providing a piercing member or tip for piercing through tissue (e.g., as shown in FIG. 1B). The snare may be energized, and/or the protrusion or piercing member or tip may have a concentrated electron or energy density, allowing the piercing member to pierce through tissue. Optionally, the protrusion may be sharpened or pointed to facilitate mechanical piercing or cutting.

The protrusion may be advanced through an extra-anatomic opening created in the airway wall. Optionally, the protrusion may be advanced to the airway wall, and used to create an opening, channel or port through the airway wall. The protrusion may then be used to create an opening, channel or port through or into the parenchyma or lung tissue by advancing the protrusion through the parenchyma or lung tissue. This may be accomplished prior, during or after snare activation or expansion. The snare may be advanced out of the opening at the distal end of the elongate instrument, through the opening through the airway wall and into the parenchyma or lung tissue. The snare may be opened or expanded to create a slit in the lung tissue or to enlarge the hole or slit in the lung tissue, which was created by the protrusion. The tissue may be cut and a hole or slot or channel may be formed as the snare is advanced into the tissue and/or as the snare is pulled or retracted from the tissue. The snare may be advanced or retracted in a collapsed or expanded form.

The snare is advanced toward the target tissue mass and positioned next to, near or in the proximity of the target tissue mass. The snare is opened or expanded, if not already opened or expanded. The size of expansion can be varied to determine how much tissue is excised and expansion can take place before or during rotation. The elongate instrument and/or snare is rotated around the target tissue mass, such that the snare cuts an area or section of tissue encapsulating or enclosing the target tissue mass. Rotation of the snare causes the circular or loop shaped snare to cut a substantially spherical shaped section of tissue or ball of tissue with the target tissue mass or tumor located within the cut section of tissue, e.g., in the center of the cut section of tissue. Cutting performed by the protrusion and/or snare or loop may be performed by activating energy delivery to perform energy based cutting or by providing a sharpened or cutting surface or edge on the snare to perform mechanical cutting.

After turning off energy delivery, the snare may be closed down or cinched around the cut section of tissue or spherical shaped cut section of tissue, encapsulating the target tissue mass such that the snare holds and/or compresses the cut tissue and the target tissue mass is encapsulated therein. The snare may be retracted or pulled out of the tissue, removing the excised or cut tissue mass from the parenchyma or lung tissue, through the opening through the airway wall and out of the patient. Removal of the target tissue or tumor, which is enclosed or encapsulated within healthy or normal tissue, may avoid or minimize tracking or seeding of any cancerous, tumor or diseased tissue from the target tissue mass or tumor in the patient. In certain variations, suction may be utilized to remove the cut section of tissue.

In one example, a snare may be positioned in tissue adjacent to or next to a target tissue or tumor, rather than through the target tissue, and as the snare is expanded or opened, the snare cuts through the adjacent tissue making a track or slit in the tissue. The snare may be expanded to a diameter having a size sufficient such that upon subsequent rotation of the expanded snare about a point outside or next to the target tissue, the snare will cut tissue around the target tissue. For example, the snare may be rotated about ninety degrees or any degree necessary to form a cut or track around the target tissue and then the snare may be closed or collapsed to complete the cut or track excision. This results in a cut out section of healthy tissue which fully encases or protects the target tissue or tumor within healthy or normal tissue. The snare may be re-expanded and positioned around the cut section of tissue to cinch or grab the cut section of tissue for removal. Optionally, suction may be utilized to remove the cut section of tissue.

Lung tissue is very compressible because there is a large amount of air in the lung. Cinching the snare down around the excised section of tissue may compress the tissue. Also, as the excised tissue is pulled through the opening through the airway wall, the opening tends to provide give or to expand. Thus, a large amount of inflated excised tissue may be removed through an opening in an airway wall that has a smaller diameter than the diameter of the inflated excised tissue by compressing the excised tissue and allowing the opening in the airway wall to expand. For example, a one centimeter tumor may be compressed and pulled out of an opening or hole in an airway wall, where the opening or hole is half a centimeter in size, i.e., half the size of the tumor or even smaller. The expandability of the tissue through which the excised tissue mass is being removed may be a factor in determining the size of the opening necessary to remove the tissue mass.

Optionally, vacuum may be applied to the excised tissue to compress and/or suck or draw down the excised tissue for removal. For example, suction may compress or pull the excised tissue down to about 10 to 1 from 8 to 1. In certain variations, suction or vacuum may be applied through an opening at the distal end of the elongate instrument.

As discussed supra, a rigid septum provided at the opening at the distal end of the elongate instrument may provide support to keep the first and second portion, members or legs of a snare or wire loop separated from one another and prevents the snare from collapsing and twisting on itself when the snare is rotated or otherwise actuated. If the snare were to collapse or twist into a spiral, energy or electrical current flow through the snare would stop, which would disrupt the ability of the snare to cut or excise tissue.

In certain variations, a bag or sleeve may be provided for catching the excised tissue as it is removed from the surrounding tissue, e.g., in the lung. For example, a bag or sleeve may be positioned at the distal end of the elongate instrument for receiving the excised tissue as it is pulled from the parenchyma or surrounding lung tissue by the snare. Similarly, a sheet of material may be unfurled from one side of the snare loop as it rotates around tissue, thereby fully encapsulating the tissue before it is withdrawn from the body.

In certain variations, a sealant may be delivered via the lumens, ports, or openings in the elongate instrument or the snare or from spines along the outside of the elongate instrument or snare. The sealant may be delivered in the slit or incision formed by the snare or protrusion to seal blood vessels or air leaks. For example, sealant may be delivered as the snare is being retracted from the lung tissue during removal of the excised section of tissue. Optionally, a blunt tipped extension or member may be used to compress airways to stop air leaks.

Where excision is performed on tissue in the lung, the lung is a low pressure system which facilitates sealing of blood vessels that may be cut during the excision process. The energy that is used to power the snare to cut tissue may also be used (by changing the wavelength, power, voltage, current, or wave form) to apply heat to seal the cut vessels.

In certain variations, various excision methods and apparatus described herein may be guided to or may access a target tissue or tumor by being advanced into and through an airway, through an opening or extra-anatomic opening created in an airway wall and to the target tissue or tumor beyond, at or near the created opening, where the target tissue is located in the lung, outside the lung or in another area of the body. The various excision apparatus described herein, may be guided or navigated to the target tissue or tumor and/or the target tissue or tumor may be located using one or more imaging technologies, such as, x-ray, CT, MRI, fluoroscopy, 3D fluoroscopy In certain variations, methods or platforms for accessing target tissues (e.g., diseased tissue, tumors, parenchyma or other tissues or structures) in a lung or other area of the body, through an opening, extra-anatomic opening or port through the airway wall may be utilized to access a target tissue with any of the excision apparatus or methods described herein. The target tissue may be located outside of the airway in which the opening is created or beyond the airway wall, e.g., in the parenchyma of the lung.

Access to the central airways may be achieved by using a standard bronchoscope or other scope or elongate instrument. A target site or point in a larger airway or central airway or smaller airway may be determined or selected, which may allow a straight or substantially straight tunnel, channel or path to be created leading directly to the target tissue. Once the target site on the airway wall is located an opening is created through the airway wall at the target site on the wall by advancing a piercing member or needle to the target site and through the airway wall at the target site. The created opening may be dilated with a balloon catheter or other expandable device.

Once the opening has been dilated, a sheath or other elongate instrument may be fed through the hole or opening and into the lung tissue. The sheath may contain a dissecting catheter and the tip of the dissecting catheter may be sharp to tunnel through tissue or it may be blunt or rounded to allow it to tunnel without perforating blood vessels or other structures. The tip may tunnel or advance through the lung tissue in a substantially straight path where turns are minimized or eliminated. Once the sheath and dissecting catheter are fed to or near the target tissue or tumor, the dissecting catheter may be removed, with the sheath remaining in position to be used to access the target tissue or tumor and to deliver any of the various excision apparatus described herein to or near the target tissue or tumor to perform excision. Various imaging techniques may be utilized to guide the bronchoscope and piercing member and to guide the sheath, dissecting catheter, and/or excision apparatus through the airway to the target site on the airway wall and/or to the target tissue for removal. Imaging techniques may include fluoroscopy, computed tomography, positron emission technology, magnetic resonance imaging, or ultrasound.

In certain variations, the multiple steps of the above procedure, i.e., creating an opening in the airway wall, going through the opening to dilate it and/or extending an instrument or apparatus through the opening to access a target tissue for excision, may be performed with a single device or with more than one device. For example, a multi purpose device, e.g., a variation of an excision apparatus as described herein, may create an opening with an energized protrusion or piercing tip, and be advanced through the opening to dilate the opening and/or access a target tissue to perform excision. Alternatively, the above procedure may be performed with more than one device, e.g., utilizing separate devices to create an opening, to dilate the opening and/or access the target tissue via the created opening with an excision apparatus (as described herein) to excise or cut tissue.

The various excision methods or apparatus described herein may also be guided to or may access a target tissue or tumor using any of the various devices or methods for creating an extra-anatomic opening in an airway wall and/or accessing tissue through an extra anatomic opening through an airway wall as described in the following: U.S. Pat. Applications: 61/485,621, filed on May 13, 2011; Ser. No. 13/107,720, filed on May 13, 2011; Ser. No. 13/107,759, filed on May 13, 2011; 61/563,369 filed Nov. 23, 2011; Ser. No. 11/538,950 filed Oct. 5, 2006; Ser. No. 12/939,968 filed Nov. 4, 2010; Ser. No. 12/939,961 filed Nov. 4, 2010; and Ser. No. 12/939,956 filed Nov. 4, 2010; the contents of each of which are incorporated herein by reference in their entirety.

Also, in certain variations, any of the imaging technologies described above may be incorporated into an excision apparatus or may be performed through the elongate instrument of the apparatus such that navigation or tracking, tissue cutting, and tissue removal may be performed by a single device or multiple devices provided via the elongate instrument or other instrument.

Figure 3A:
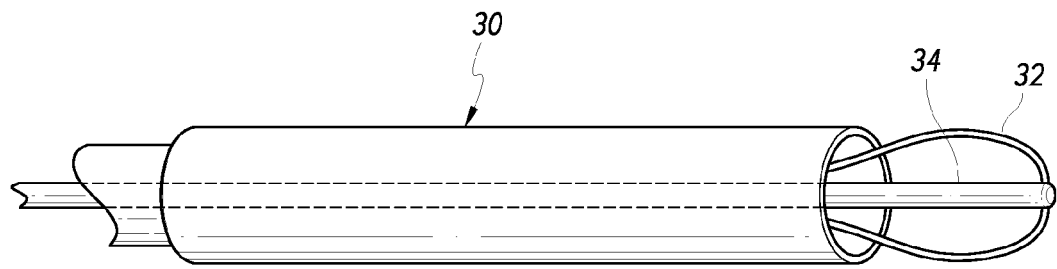
FIG. 3A illustrates a side view of another variation of an apparatus for excising tissue.
Figure 3B:
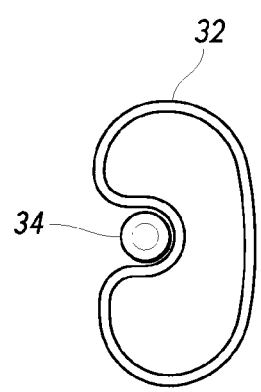
FIG. 3B illustrates a front view of the apparatus for excising tissue of FIG. 3A.

As shown in FIGS. 3A-3B, another variation of an apparatus for excising tissue may include an elongate instrument 30 and a snare 32 or cutter loop extending from or positioned at an opening at the distal end of the elongate instrument 30. A rod 34, which may be positioned in or extend from the elongate instrument, may be connected or attached to the distal end of the snare 32. In use, the elongate instrument 30 may be advanced to, near or in proximity to the target tissue mass. The snare 32 may be advanced such that it cuts through tissue and positions the snare 32 next to the target tissue mass. In certain variations, where the apparatus is used to excise tissue from a lung, e.g., a lung tumor, the apparatus may be advanced within an airway of the lung. The snare 32 may cut or create an opening through the airway wall and may be advanced or pushed out, into the parenchyma or lung tissue, to or near the target tissue mass.

Once positioned near the target tissue mass, the rod 34 may be actuated or withdrawn, pulling the snare 32, from the snare distal end, such that the snare 32 folds back on itself, thereby cutting an area or section of tissue surrounding the target tissue mass. The cut section of tissue encapsulates or encloses the target tissue mass or tumor and cuts of any blood vessels leading to the target tissue mass or tumor. The snare 32 may then be reopened or unfolded such that the snare may surround the cut section of tissue. The snare 32 may then be drawn down or cinched around the cut section of tissue to grab or hold the tissue. The snare 32 may then be retracted to remove the cut section of tissue from the lung and from the patient, e.g., via the opening through the airway wall. Optionally, the cut section of tissue may be left in place to shrivel and die in the body as the blood vessels and blood supply to the section of tissue have been cut off and no longer feed the tissue. Rotation of the snare may or may not be required to effect cutting of the tissue by the snare 32.

Figure 5A:
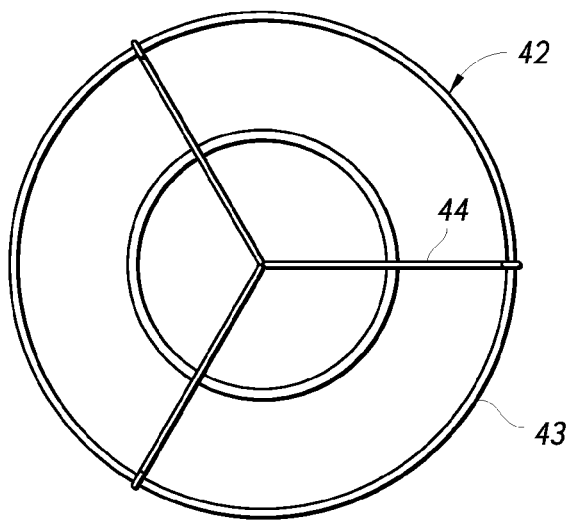
FIG. 5A illustrates a side view of another variation of an apparatus for excising tissue.
Figure 5B:
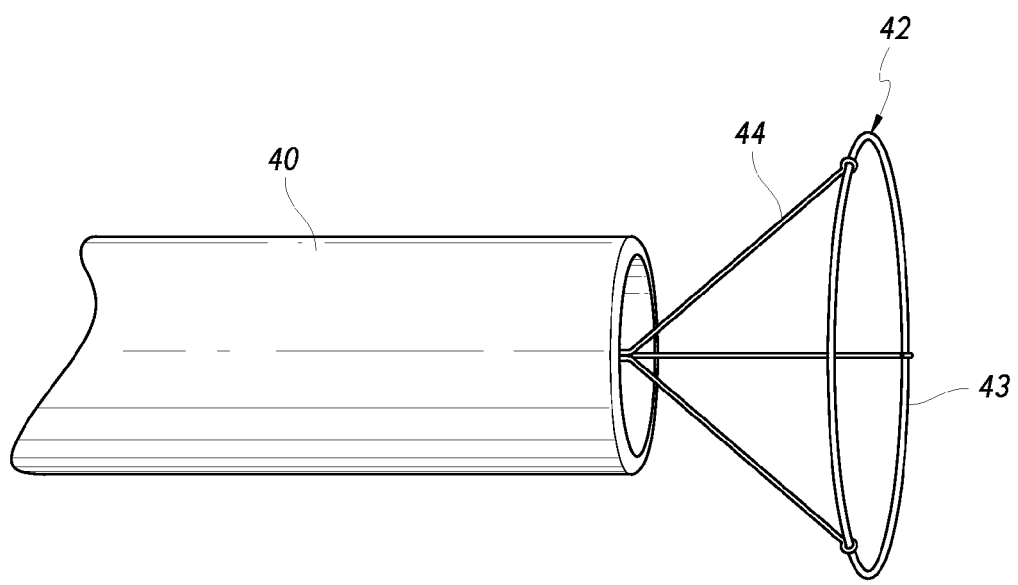
FIG. 5B illustrates a front view of the apparatus for excising tissue of FIG. 5A.

FIGS. 5A-5B show another variation of an apparatus for excising tissue including an elongate instrument 40 and a cutter in the form of a snare 42. The snare 42 includes a loop 43 and one or more portions, members or legs 44. The legs 44 connect to various points along the loop 43. The legs 44 expand or hold open the loop 43. In use, the snare 42 is advanced from the elongate instrument and pushed over and around a target tissue mass, with the loop advancing past the target tissue mass. As the snare 42 is advanced, it cuts a section of tissue around the target tissue mass. The cut section of tissue encapsulates or encloses the target tissue mass. Once the loop 43 is advanced over and passed the target tissue mass, the legs 44 are drawn toward each other or collapsed, flexing the legs 44 and closing the snare 42 around the cut section of tissue. This forms a cage or capsule around the cut section of tissue such that the snare may hold the cut section of tissue. The snare may be retracted or withdrawn to remove the cut section of tissue and the target tissue mass encapsulated therein.

In certain variations, the loop 43 may be round or configured in a variety of different shapes, such that the snare may be collapsed and positioned within a lumen of the elongate instrument. In certain variations, a lumen or working channel of the elongate instrument may have a diameter that measures about 1 to about 5 mm, e.g., 2.4 mm.

The legs, members or portions of a snare may be insulated in a nonconductive material for snares that are energized to perform electrical cutting. Optionally, a sealed sack or sheet may be positioned around the legs, such that when the legs are collapsed and the snare is closed down, the sealed sack or sheet would be wrapped around the snare and/or the cut tissue. Optionally, the snare may be configured for mechanical cutting, e.g., where the snare has a sharpened edge or blade.

Figure 4A:
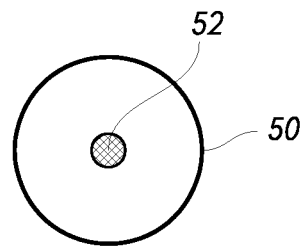
FIGS. 4A-4B illustrates various shapes of cut tissue encapsulating a target tissue mass or tumor for removal.
Figure 4B:
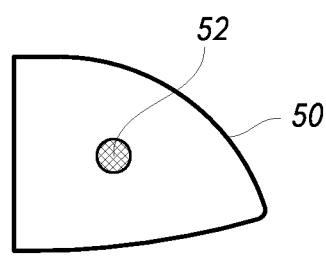

As shown in FIGS. 4A-4B, the various apparatus and methods described herein may cut a section of tissue 50 encapsulating a target tissue mass 52, where the cut section of tissue 50 has a variety of shapes and configurations depending on the apparatus utilized and the shape or configuration of the cutter, e.g., a snare or loop or other cutting mechanism.

Figure 6A:
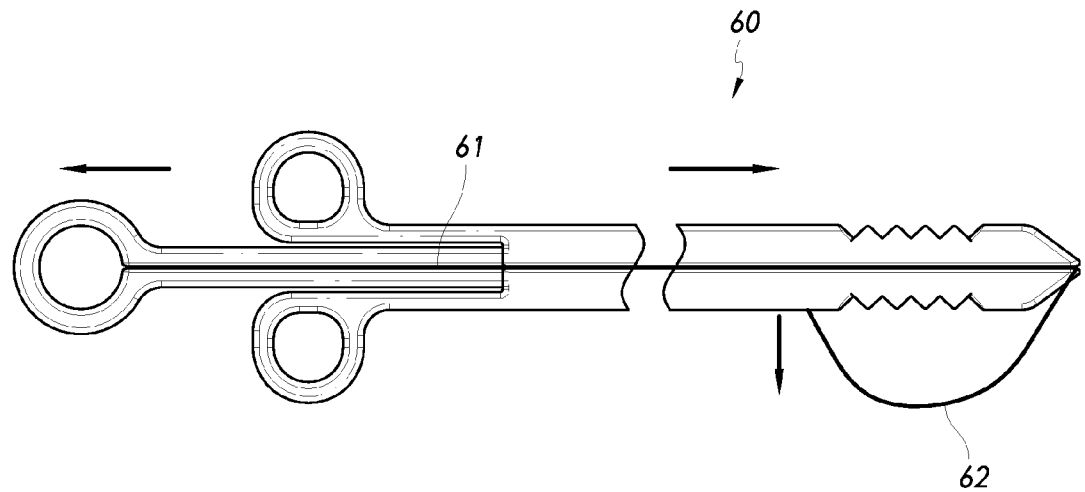
FIGS. 6A-6B illustrate a side view of a variation of an apparatus for excising tissue having a side cutter.
Figure 6B:
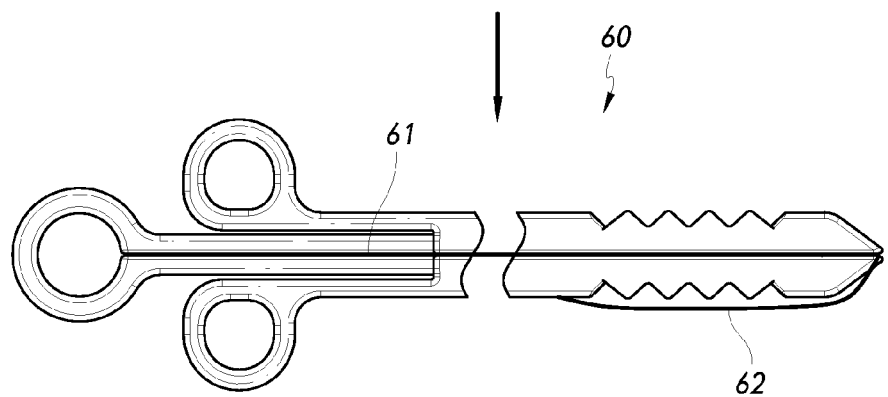

FIGS. 6A-6B show another variation of an apparatus 60 for excising tissue. The apparatus 60 includes a side cutter 60. In this embodiment, first and second members 61, 62 are positioned at the distal end of the apparatus. The first member 61 is more rigid than the second member 62 and is slidably actuatable along the axis of the apparatus 60. The second member 62 member is less rigid so when the first member 61 is pulled in a proximal direction, the second member 62 deploys outward to form a cutting snare (for example, the second member 62 may be a wire or cable). In this way, the cutting apparatus 60 can be electrically energized in the closed position, pushed forward, cutting through tissue to be located next to a target tissue mass, actuated to deploy (expand) the snare while energized, and rotated while energized to cut around the target tissue mass to cut or excise the tissue. Once the tissue mass encasing the target tissue mass has been excised, the snare can be rotated back to straddle the center of the tissue mass, electrical energy can be turned off, and the snare can then be drawn down to compress the mass for removal from the body. The amount of deployment or expansion can be varied as the snare is rotated to determine how much tissue is excised. For example, if the apparatus is placed next to the tissue mass to be excised, the user might start rotationally cutting with the snare collapsed, gradually deploying the snare as it is rotated to 180 degrees, and then gradually collapse the snare as it rotates through the final 180 degrees of rotation to achieve cutting only around the mass. Alternately, if the apparatus was placed in the center of the mass, the snare could be deployed to a specific size as it is rotated through 360 degrees to cut around the mass.

Electrical cutting or mechanical cutting may be utilized in any of the variations described herein. A cutter may be energized to cut tissue. Optionally, a cutter may include a sharp edge or may utilize ultrasound to cut tissue. In certain variations, ultracision or a rotary ultracision may be utilized to cut tissue. For example, an ultrasonically rotating cutter which may rotate in small degree intervals to create a cutting action may be utilized.

Any of the variations described herein may used for cutting or excising tissue in any region of the body, e.g., the lung, liver, or brain via various access points, utilizing minimally invasive or open surgery techniques.

All publications, patent applications, patents, and other references mentioned herein are incorporated by reference in their entirety. To the extent there is a conflict in a meaning of a term, or otherwise, the present application will control. Although variations of the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. It is also contemplated that combinations of the above described embodiments/variations or combinations of the specific aspects of the above described embodiments/variations are within the scope of this disclosure.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

I claim:

1. A method of excising a target tissue mass from a subject, the method comprising:
   advancing an elongate instrument having an opening at its distal end through the airways of a lung of the subject, wherein a proximal section of the elongate instrument is flexible;
   advancing a snare from the distal end of the elongate instrument, wherein the snare is configured to cut tissue;
   positioning the snare near the target tissue mass, wherein the snare is positioned in healthy tissue adjacent the target tissue mass;
   actuating the snare to cut a section of healthy tissue encapsulating the target tissue mass, wherein the snare is expanded and rotated thereby cutting around the target tissue mass and collapsed to complete the cut, thereby creating a cut section of healthy tissue which fully encases the target tissue mass;
   applying suction to remove air from the cut section of healthy tissue sufficiently causing compression of the cut section of healthy tissue; and
   securing the cut section of tissue and the target tissue mass encapsulated therein with the snare and removing the cut section from the subject.

2. The method of claim 1, further comprising closing the snare around the cut section of tissue such that the snare holds the cut section of tissue and the target tissue mass encapsulated therein for removal.

3. The method of claim 1, wherein the cut section of tissue and the target tissue mass encapsulated therein are removed by retracting the snare into the elongate instrument.

4. The method of claim 1, where the cut section of tissue is captured by collapsing the snare around the cut section of tissue and extracting the cut section of tissue by removing the snare from the subject.

5. The method of claim 1, wherein the snare cuts a slit through tissue as it is advanced from the elongate instrument and into position next to the target tissue mass.

6. The method of claim 1, further comprising delivering a sealant to seal cut airways or blood vessels.

7. The method of claim 1, further comprising applying suction through the elongate instrument to compress or draw down the cut section of tissue for removal.

8. The method of claim 1, wherein the snare is reexpanded to positioned in healthy tissue next to the target tissue and the cut section of tissue comprises healthy tissue encasing the target tissue mass.

9. The method of claim 1, wherein the target tissue mass is a lung tumor.

10. The method of claim 1, wherein the snare is advanced through an opening through an airway wall of an airway located in the lung to access the target tissue mass or tumor in the lung.

11. The method of claim 1, wherein the snare is configured to collapse around the cut section of tissue to hold the tissue for removal.

12. The method of claim 1, further comprising unfurling a sheet of material from a side of the snare when the snare is rotated around the target tissue mass such that the target tissue mass is fully encapsulated.

13. The method of claim 1, wherein the snare comprises a loop, wherein the loop is perpendicular to the elongate instrument, and wherein a plurality of legs extend from the distal end of the elongate instrument and attach to the loop.

14. The method of claim 1, wherein the cutting around the target tissue mass comprises electrical cutting.

15. The method of claim 1, wherein the creating the cut section of healthy tissue which fully encases the target tissue mass cuts all sides of the target tissue mass.

16. The method of claim 1 comprising applying suction to remove the cut section of tissue.

17. A method of excising a target tissue mass from a subject, the method comprising:

advancing an elongate instrument having an opening at its distal end through the airways of a lung of a subject, wherein a proximal section of the elongate instrument is flexible;

advancing a snare from the distal end of the elongate instrument, wherein the snare is configured to cut tissue;

positioning the snare in adjacent tissue surrounding the target tissue mass;

cutting around the target tissue mass, wherein the cutting is at least partially performed by expanding and rotating the snare;

collapsing the snare to complete the step of cutting, thereby creating a cut tissue section which fully encases the target tissue mass; and re-expanding the snare to secure the cut tissue section and the target tissue mass encapsulated therein and removing the cut section from the subject.

* * * * *